(12) United States Patent
Strube et al.

(10) Patent No.: US 9,994,733 B2
(45) Date of Patent: Jun. 12, 2018

(54) METHOD FOR COATING SURFACES BY ENZYMATIC REACTION

(71) Applicant: UNIVERSITÄT PADERBORN, Paderborn (DE)

(72) Inventors: Oliver Ingolf Strube, Paderborn (DE); Wolfgang Bremser, Paderborn (DE); Arne Alexander Rüdiger, Paderborn (DE)

(73) Assignee: Universität Paderborn, Paderborn (DE)

( * ) Notice: Subject to any disclaimer, the term of this patent is extended or adjusted under 35 U.S.C. 154(b) by 0 days. days.

(21) Appl. No.: 15/129,468

(22) PCT Filed: Mar. 31, 2015

(86) PCT No.: PCT/EP2015/056995
§ 371 (c)(1),
(2) Date: Sep. 27, 2016

(87) PCT Pub. No.: WO2015/150368
PCT Pub. Date: Oct. 8, 2015

(65) Prior Publication Data
US 2017/0121558 A1 May 4, 2017

(30) Foreign Application Priority Data
Apr. 4, 2014 (DE) .................... 10 2014 104 859

(51) Int. Cl.
*A61K 9/00* (2006.01)
*C09D 189/00* (2006.01)
(Continued)

(52) U.S. Cl.
CPC ........... *C09D 189/005* (2013.01); *C09D 5/00* (2013.01); *C09J 11/00* (2013.01); *C09J 189/005* (2013.01);
(Continued)

(58) Field of Classification Search
CPC .................................................. C09D 189/005
See application file for complete search history.

(56) References Cited

U.S. PATENT DOCUMENTS 3,323,929 A * 6/1967 Salzberg ............... D21H 19/50
106/157.71
4,762,868 A 8/1988 Wright
(Continued)

FOREIGN PATENT DOCUMENTS

EP 0839498 A1 5/1998
WO 9607444 A1 3/1996
(Continued)

OTHER PUBLICATIONS

Notification Concerning Transmittal of International Report on Patentability dated Oct. 13, 2016; 8 pages.
(Continued)

*Primary Examiner* — Paul Dickinson
(74) *Attorney, Agent, or Firm* — Reising Ethington P.C.

(57) ABSTRACT

The invention relates to a method for coating surfaces by enzymatic reaction of a biopolymer, wherein the method comprises the following steps: a) applying an enzyme to the surface of a substrate, and b) contacting the enzyme with the biopolymer to be deposited, wherein the enzyme cleaves the biopolymer, wherein the cleavage gives rise to at least two cleavage products of the biopolymer having different solubility in a solvent, and at least one cleavage product of the biopolymer having relatively low solubility is deposited on the surface of the substrate, and to a coated article obtainable by the method and to a coating composition comprising a biopolymer and at least one component selected from the group comprising binders, fillers, pigments and/or additives, and optionally a solvent.

11 Claims, 6 Drawing Sheets

(51) Int. Cl.
  *C12N 11/14* (2006.01)
  *C12N 9/64* (2006.01)
  *C09D 5/00* (2006.01)
  *C09J 11/00* (2006.01)
  *C09J 189/00* (2006.01)

(52) U.S. Cl.
  CPC ............ *C12N 9/6483* (2013.01); *C12N 11/14* (2013.01); *C12Y 304/23004* (2013.01)

(56) References Cited

U.S. PATENT DOCUMENTS

| | | | |
|---|---|---|---|
| 5,660,873 A * | 8/1997 | Nikolaychik | ........... A61L 31/10 427/2.24 |
| 2002/0054914 A1 | 5/2002 | Morcol et al. | |
| 2009/0042218 A1 | 2/2009 | Ikebukuro et al. | |
| 2009/0275079 A1 * | 11/2009 | Edens | ........................ C12N 9/62 435/69.1 |
| 2010/0143738 A1 * | 6/2010 | Bloembergen | ........... B29B 7/42 428/537.5 |
| 2013/0065291 A1 * | 3/2013 | Jia | ........................ C09D 189/00 435/180 |
| 2013/0309172 A1 | 11/2013 | Berlin et al. | |

FOREIGN PATENT DOCUMENTS

| | | |
|---|---|---|
| WO | 9959647 A1 | 11/1999 |
| WO | 2005076987 A2 | 8/2005 |

OTHER PUBLICATIONS

B. Müller, U. Poth, "Lackformulierungen und Lackrezeptur", 3rd edition 2009, Vincentz Network. pp. 18-23 and 40-43.
"Coatings Formulation", 2nd Revised Edition 2011, Vincentz Network. pp. 20-24 and 40-43.
International Search Report for PCT/EP2015/056995; Jun. 8, 2015; 6 pages.

* cited by examiner

METHOD FOR COATING SURFACES BY ENZYMATIC REACTION

The invention relates to the field of biological coatings. More particularly, the invention relates to the coating of surfaces with biopolymers via an enzymatic reaction.

Biopolymers as coating materials have advantageous properties for many applications, for example with regard to biocompatibility, multifunctional surfaces and biodegradability. In recent years, research in the area of biopolymers has greatly intensified; in this connection, the application of biopolymers to solid substrate surfaces continues to be of key interest. To date, biological coatings have been produced similarly to polymer coatings using classic paint-chemistry methods. However, these coating methods, such as a spray-, dip- or spin-coating method, allow only little control over the film formation or an application of complex coatings. Structures can only be generated in the macroscopic range, for example by means of a masking element. However, this requires a multiplicity of method steps and the use of different methods for the control of the film properties. There is therefore a need for the further improvement of the production of coatings with biopolymers.

Document WO 2005/076987 discloses the possibility of an enzyme-controlled coating of medicaments, though there is no disclosure of how such a coating might be applied.

It is therefore an object of the present invention to provide a method for producing a coating with biopolymers by using enzymes. More particularly, it is an object of the present invention to provide a method which allows a specific coating.

This object is achieved by a method for coating surfaces by enzymatic reaction of a biopolymer, wherein the method comprises the following steps:
a) applying an enzyme to the surface of a substrate, and
b) contacting the enzyme with the biopolymer to be deposited, the enzyme cleaving the biopolymer, the cleavage giving rise to at least two cleavage products of the biopolymer having differing solubility in a solvent, and at least one cleavage product of the biopolymer having relatively low solubility being deposited on the surface of the substrate.

It was found that, surprisingly, it is possible to utilize an enzymatic reaction in order to trigger a deposition process. Advantageously, it is possible to utilize the enzymatic reaction for the specific control of the film properties at the molecular level. For instance, the control of film properties such as layer thickness and film structure and also the specific coating of individual regions of a substrate are made possible. By means of the method according to the invention, the precise coating of objects of complex geometry with biological films is made possible. In a single process, it is possible to realize a high variability of various film parameters. This provides an immense increase in efficiency of coating methods and a simple achievability of complex film properties. Advantageously, the deposition of biopolymers further allows the production of biocompatible coatings and of biodegradable coatings.

The term "biopolymer" is to be understood in the context of the present invention to mean polymers of biological origin. Polymers synthesized by living organisms are, for example, polysaccharides and proteins. For instance, proteins can be understood as polymers formed of amino acid monomers.

Preferred biopolymers are proteins. Proteins can be present as isolated proteins or in the form of a protein complex or as a mixture of similar or different proteins. Enzymes which can cleave biopolymers are, in particular, proteases. In preferred embodiments, the biopolymer is therefore a protein, protein complex or protein mixture and the enzyme is a protease. Many polymer/protease reactions are known and the corresponding proteins and proteases are commercially available or isolatable by known means.

A protease-induced cleavage of a biopolymer gives rise to at least two cleavage products, the number of cleavage products being dependent on the number of sites of the biopolymer which are recognized and cleaved by the corresponding protease. Depending on the nature of the biopolymer, the cleavage products may have different properties, for example a differing solubility in a solvent. The cleavage of a protein can, for example, give rise to a molecular part having relatively high hydrophilicity and thus increased solubility in an aqueous solvent and a molecular part having relatively high hydrophobicity and thus relatively low solubility in an aqueous solvent. When the hydrophobicity of a cleavage product of the protein in an aqueous solvent is sufficiently high and said cleavage product is situated close to a surface, the hydrophobic cleavage product or the cleavage product of the biopolymer having relatively low solubility can be deposited on the surface of the substrate. During the contacting of the enzyme with the biopolymer to be deposited, the biopolymer is preferably present in solution. A preferred solvent is water. An aqueous solution can be a solution of the biopolymer in water or in an aqueous mixture.

A preferred protein is casein. Casein is present in milk or aqueous solvents in the form of micelles, which are mainly formed of four casein proteins, $\alpha_{S1}$-casein, $\alpha_{S2}$-casein, $\beta$-casein and $\kappa$-casein. Casein can thus also be considered to be a mixture of proteins. Simple models of the casein structure assume that the core of the micelle is mainly formed of the hydrophobic $\alpha_{S1}$-casein, $\alpha_{S2}$-casein and $\beta$-casein, whereas the amphiphilic $\kappa$-casein accumulates on the external surface of the micelle. The protease chymosin cleaves $\kappa$-casein at the site of the phenylalanine[105]-methionine[106] bond. As a result, a hydrophilic part (caseinomacropeptide) is cleaved off, whereas a hydrophobic part called para-$\kappa$-casein remains in the micelle. This results altogether in a higher hydrophobicity of the micelles, which can agglomerate and precipitate from, for example, milk or aqueous solvents.

In a preferred embodiment, the protein is casein and the protease is selected from the group comprising chymosin and/or pepsin. Chymosin is a so-called aspartyl or carboxyl protease, which can cleave the peptide bonds of a protein with consumption of a molecule of water. The enzymatic cleavage of casein by chymosin utilizes the complex structure of the casein micelles and the cleavage-altered solubility of the micelles in order to form a coating as a result of deposition of the micelles, which are more hydrophobic after the cleavage. In another embodiment, the protein is fibrinogen and the protease is thrombin. In these embodiments, the contacting of the enzyme with the biopolymer to be deposited leads to the enzyme cleaving the biopolymer into a hydrophilic and a hydrophobic part and the hydrophobic part being able to be deposited on the substrate. A further advantage provided by a coating with chymosin-cleaved casein is the higher hydrophobicity and thus higher stability of the casein coating with respect to water in comparison with coatings with noncleaved casein.

Owing to the enzyme applied according to the invention on the surface of a substrate, the cleavage of the biopolymer takes place on the surface of the substrate or in the immediate vicinity thereof. The size or extent of the reaction area in which the enzyme can contact the biopolymer, on or above the surface, can be varied by means of the technique for immobilizing the enzyme onto the substrate surface. In preferred embodiments of the method, the enzyme is applied to the surface by means of physical adsorption, or ionic, coordinate or covalent bonding. It is possible to effect the covalent bonding to the surface via a polymeric spacer preferably selected from the group comprising polyethylene glycol, polyvinyl alcohol, polyesters and/or dextrans. It was possible to demonstrate bonding of chymosin to a glass surface via polyethylene glycol as polymeric spacer.

Depending on the nature and strength of the bonding of the enzyme to the surface, said enzyme may possibly diffuse from the surface into a surrounding solvent. The enzyme diffusion area determines the extent of the reaction area in which a cleavage of the biopolymer can take place. For a controlled deposition, it is advantageous for the cleavage of the biopolymer to take place close to the surface, and so the cleavage products of the biopolymer having relatively low hydrophilicity are deposited on the surface of the substrate and do not, as is possible in the case of the casein micelles, agglomerate at a relatively great distance from the surface and precipitate in the solution. This can be provided by a physical adsorption, ionic bonding, coordinate bonding or covalent bonding of the enzyme to a surface.

A preferred embodiment is the physical adsorption of the enzyme to the substrate surface. A physical adsorption can, for example, be achieved by dripping of a solution of the enzyme onto the surface and surface-drying. A physical adsorption can provide a diffusion of the enzyme into the surrounding solvent. For example, the water-soluble chymosin can diffuse into the solution. Owing to this mobility of the enzyme, a reaction with the biopolymer can take place on the surface and also in the diffusion area above the surface. This reaction zone enlarges with increasing reaction time. As a result, the reaction of the enzyme with the biopolymer is effected so long as noncleaved biopolymer is available. The reaction is not self-terminating insofar as the enzyme on the surface is not altogether covered by deposited cleavage products and thus inactivated. This makes it possible to influence, for example, the layer thickness by varying the reaction parameters such as reaction time and/or reaction temperature. A high enzyme concentration and good conditions for the enzyme activity can lead to a quickened and/or increased layer formation. Generally, multilayer or relatively thick coatings lead to a better stability. In the case of casein, it was possible to demonstrate that the physical adsorption of chymosin to glass surfaces led to continuous casein films having a variable layer thickness and degree of coalescence.

A further preferred embodiment is a covalent bonding of the enzyme to the surface. A covalent immobilization without a spacer allows only little enzyme mobility. As a result, a reaction with biopolymer can only take place directly on the surface. Owing to deposited cleavage products, the enzyme on the surface is covered and is not available for further cleavage reactions. The reaction is thus self-terminating and can provide thin coatings. For instance, in the case of casein, it was possible to produce a monomicellar coating by means of covalent bonding of chymosin to a surface. A covalent bonding of an enzyme can be provided via a functionalization of the surface. In the case of a functionalization of the surface, specific, reactive functional groups to which enzymes can bind in a specific and selective manner are bonded on the surface. For example, glass surfaces can be functionalized with amino or epoxy groups by means of silanes.

Depending on the nature of the application of enzyme, a coating can be applied in a continuous manner or on defined regions of the surface. In embodiments of the method, the enzyme is applied to the surface in a full-area or partial manner. Especially by means of covalent immobilization of an enzyme on a surface, it is possible to provide a selective or partial coating, since cleavage products are formed and deposited only in regions of applied enzyme. This allows the production of complex and structured coatings. Advantageously, it was possible to demonstrate that, by means of a deposition of very small enzyme aggregates, a deposition of individual particles of casein can be achieved.

Altogether, the method according to the invention can provide a wide range of possibilities for a controlled deposition of protein coatings. Especially through the use of enzymes in the direct vicinity of the substrate surface, the cleavage and deposition take place in the immediate of the substrate and individual regions can be coated in a specific manner and with control of the film properties. The method allows a regulation of the deposition process, which regulation is not achievable with conventional deposition methods. Furthermore, the use of biobased materials is advantageously raw-material-conserving, nontoxic and allows, in the case of covalent immobilization, a reusability of the precursor solutions.

Method parameters such as the concentration of the enzyme and of the biopolymer, the reaction time and the temperature at which the deposition reaction is carried out can be varied depending on the desired layer and/or layer thickness. In preferred embodiments of the method, the biopolymer to be deposited can be present in aqueous solution, the concentration of the biopolymer in the solution being by preference within the range from $\geq 0.01$ g/L to $\leq 50$ g/L, preferably within the range from $\geq 0.1$ g/L to $\leq 10$ g/L. Furthermore, the reaction time between biopolymer and enzyme can be within the range from $\geq 1$ min to $\leq 240$ min, preferably within the range from $\geq 5$ min to $\leq 60$ min. Furthermore, the temperature of the deposition reaction can be within the range from $\geq 0°$ C. to $\leq 50°$ C., preferably within the range from $\geq 30°$ C. to $\leq 40°$ C. It was possible to establish that said method parameters led to good results.

By appropriate selection of the application of the enzyme and of the method parameters, it is possible to produce coatings having variable layer thickness. In embodiments of the method, a coating having a layer thickness within the range from $\geq 10$ nm to $\leq 50$ µm, preferably within the range from $\geq 20$ nm to $\leq 1$ µm, can be applied. Such layer thicknesses are highly suitable for applications as a coating of medical implants, biodegradable materials, edible materials, colloidal particles or as adhesive bonding of surfaces to be adhesively bonded. It was possible to achieve a deposition of very thin monolayers of casein. The layer thickness can be within the range from $\geq 30$ nm to $\leq 300$ nm.

Enzymes can be applied to a multiplicity of different surfaces by means of adsorption, ionic bonding, coordinate bonding or covalent bonding. Advantageously, it is possible to coat various materials using the method according to the invention. In embodiments, the surface of the substrate can be formed of glass, plastic, metal, wood or ceramic. The method according to the invention is suitable for the coating of different substrates, for example for the coating of medical implants, or colloidal particles. Especially substrates having complex geometry such as small medical implants are coatable with biopolymers by means of the method.

The invention further provides a coated article obtainable by means of the method according to the invention. The method according to the invention can provide a substrate or an article which is provided with a biocompatible and/or biodegradable coating. More particularly, the article can be a medical implant, a biodegradable material, an edible material, a colloidal particle or a surface to be adhesively bonded. For example, the coated article can be a biodegradable packaging material coated with a biopolymer such as casein, or a coated edible packaging or foodstuff. A surface to be adhesively bonded can be a surface of an object, with a biopolymer such as casein being deposited onto said surface, giving rise to a connecting casein layer between two objects, which layer can act as an in situ bioadhesive. It was possible to demonstrate that glass surfaces and metal surfaces could be adhesively bonded to one another as a result of a casein layer precipitated via reaction with chymosin.

By means of the method according to the invention, it is, for example, possible to provide a biocompatible coating on an implant, which makes it possible to produce an implant having an improved tolerability owing to its biocompatibility. According to the invention, an implant is to be understood to mean a substrate suited to being implanted in a patient. Examples of implants are catheters, osteosynthesis material, endoprostheses, nails, screws and/or wires, heart valves, artificial blood vessels and shunts, facial-surgery or plastic-surgery implants, middle-ear implants or dental implants.

A biocompatible coating is advantageous especially in conjunction with a coating of objects of complex geometry in the area of medical implantology. Biodegradable coatings allow self-degradable implants. Owing to the degradability, it is, for example, possible in the case of temporary implants to dispense with a second operation to remove the implant. In the area of microtechnology too, it is possible owing to the method according to the invention to advantageously use coated articles for use in the biological sphere.

The invention further provides a coated article, wherein the article comprises a casein coating formed of casein micelles, a hydrophilic part of the κ-casein having been cleaved off at the site of the phenylalanine$^{105}$-methionine$^{106}$ bond. The coating is obtainable by means of the method according to the invention by using chymosin and/or pepsin. A casein coating formed of casein micelles, substantially comprising hydrophobic $\alpha_{S1}$-casein, $\alpha_{S2}$-casein, β-casein and para-κ-casein, the hydrophilic caseinomacropeptide having been cleaved off, can provide a higher hydrophobicity and thus higher stability of the casein coating with respect to water in comparison with coatings with non-cleaved casein. The casein coating can be applied in a full-area or partial manner, more particularly on defined regions of the surface of the article. In embodiments, the casein coating can have a layer thickness within the range from ≥10 nm to ≤50 μm, preferably within the range from ≥20 nm to ≤1 μm. More particularly, the casein coating can be a monomicellar coating.

The invention further provides a coating composition containing a biopolymer and at least one component selected from the group comprising binders, fillers, pigments and/or additives and also optionally a solvent.

The term "coating composition" is to be understood in the context of the present invention to mean a composition in liquid, paste or powder form, which, applied to a substrate or subsurface, yields a coating. The surface of the substrate can be formed of glass, plastic, metal, wood or ceramic. Preference is given to a coating composition in liquid form containing a solvent. Said composition is referred to as a coating solution. The coating solution is preferably an aqueous solution. The solvent is accordingly preferably water. The biopolymer is preferably a protein, protein complex or protein mixture. The protein can be in particular casein or fibrinogen. The concentration of the biopolymer in the coating composition, more particularly the coating solution, can be within the range from ≥0.01 g/L to ≤50 g/L, preferably within the range from ≥0.1 g/L to ≤10 g/L.

In principle, the further components of the coating composition or coating solution can be constituents known to a person skilled in the art, for example as described in B. Müller, U. Poth, "Lackformulierungen and Lackrezeptur" [Paint formulations and paint recipe], 3rd edition 2009, Vincentz Network. For example, the coating composition or coating solution can contain pigments. Preferred pigments are inorganic particles, more particularly metal oxides such as titanium dioxide. These can be present in the solution or in the coating as finely distributed or dispersed particles of a size within the range from 0.01 μm to 1 μm. It is possible to use $TiO_2$ to improve the whiteness or opacity of a coating.

The coating composition is obtainable by the biopolymer, more particularly casein, and the at least one component selected from the group comprising binders, fillers, pigments and/or additives being mixed or being dissolved or dispersed in a solvent. For example, titanium dioxide can be dispersed in a casein solution.

It is possible to use the coating composition to coat surfaces. It is possible to use especially a coating solution in methods for coating surfaces by enzymatic reaction of a biopolymer. For instance, it is possible to a) apply an enzyme to the surface of a substrate, and b) contact the enzyme with the coating solution, the enzyme cleaving the biopolymer, the cleavage giving rise to at least two cleavage products of the biopolymer having differing solubility in the solvent, and at least one cleavage product of the biopolymer having relatively low solubility being deposited on the surface of the substrate. If the coating solution contains, for example, titanium dioxide particles, they can be enveloped by deposited protein and impart a white color or a color approaching white in shade to an otherwise substantially colorless protein layer.

Examples and figures which serve to illustrate the present invention are reported below.

The figures show in this connection:

FIG. 1 shows SEM images of casein layers applied by means of adsorbed chymosin on a glass slide. FIG. 1a shows a layer applied from an aqueous casein solution containing 1 g/L casein; FIG. 1b shows a layer applied from an aqueous casein solution containing 10 g/L casein. The layer boundaries in relation to the glass surface are indicated by arrows in each case.

FIG. 2 shows EDX/SEM determinations of chymosin applied covalently on a glass slide. FIG. 2a shows the SEM image of the surface, where point 1 indicates a region of the uncoated surface and point 2 indicates a region of suspected enzyme deposition. FIG. 2b shows the EDX spectra of points 1 and 2.

FIGS. 6a, b and c each show different magnifications.

MATERIALS

Casein from cow's milk and chymosin were purchased from Sigma-Aldrich and used without any further purification. The other chemicals were purchased from Fluka, Sigma-Aldrich or ABCR and likewise used without any purification.

EXAMPLE 1

Formation of a Casein Layer by Means of Adsorbed Enzyme on a Glass Slide

Glass microscope slides (Carl Roth) were cleaned with a mixture of 70% to 30% (v/v) of sulfuric acid to hydrogen peroxide and washed with deionized water. Thereafter, a solution of 1.7 mg/ml chymosin (based on the pure enzyme) in deionized water was dripped onto the surface and dried at 20° C. The glass microscope slides containing adsorbed chymosin were each placed into an aqueous casein solution of a concentration of 1 g/L, 5 g/L or 10 g/L casein at pH 3 and 40° C. After 20, 40 or 60 minutes, the microscope slides were removed from the casein solution, washed with deionized water and dried.

The casein films obtained were examined by means of electron microscopy by using a Zeiss "Neon 40" scanning electron microscope equipped with an EDX detector. SEM images of the samples were obtained through use of the InLens detector (secondary electrons) and of the SE detector (secondary and backscattered electrons) at an accelerating voltage of 2 kV.

Figure 1:
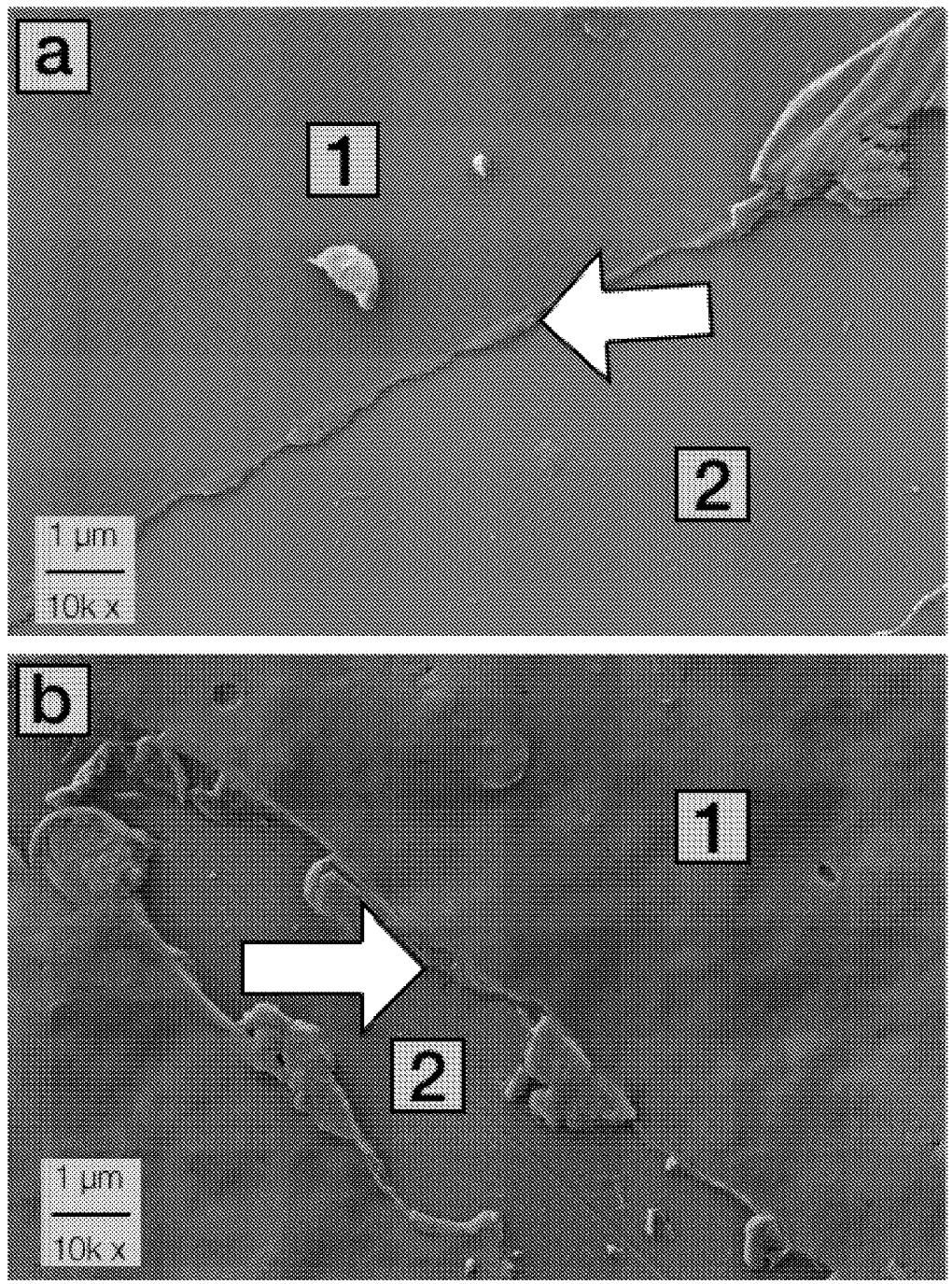

FIG. 1 shows the SEM images of the casein layer applied by means of adsorbed chymosin on glass slides. FIG. 1a shows a layer 1 applied from an aqueous casein solution containing 1 g/L casein and a reaction time of 60 minutes. Diagonally across the image, it is possible to identify a layer boundary formed by scraping-off of the casein in the upper-right region of the image. The glass surface is indicated by 2. FIG. 1b shows a layer 1 applied from an aqueous casein solution containing 10 g/L casein and a reaction time of 60 minutes. Diagonally across the image, it is possible to identify a scraped-free strip of the glass surface 2. As can be gathered from a comparison of FIGS. 1a and 1b, the applied layer from the 1 g/L casein solution was substantially thinner than the layer applied from the 10 g/L casein solution. The two SEM images each showed homogeneous films having complete coalescence of the casein micelles. On the basis of the SEM images, a thickness of the casein layer obtained was estimated within the range from 10 nm to 30 nm and from 100 nm to 250 nm, respectively.

This shows that uniform, homogeneous casein layers of variable thickness were deposited each time in the case of the concentrations and reaction times that were used. The increasing thickness of the casein layer with increasing quantity of casein and time further shows that the reaction is not self-terminating, but instead proceeds so long as adsorbed chymosin and casein micelles are available close to the surface.

EXAMPLE 2

Determination of the Stability of the Casein Coating with Respect to Water

To check the enzymatically catalyzed cleavage reaction into a hydrophilic and a hydrophobic part of the casein for the formation of the casein coating, casein coatings were applied to glass microscope slides with and without use of the enzyme.

Four glass microscope slides (Carl Roth) were cleaned with a mixture of 70% to 30% (v/v) of sulfuric acid to hydrogen peroxide and washed with deionized water. Thereafter, on two of the four glass microscope slides, a solution of 1.7 mg/ml chymosin in deionized water was dripped onto the surface and dried at 20° C. All four glass microscope slides were subsequently placed into an aqueous casein solution of a concentration of 10 g/L casein at pH 3 and 40° C. After 60 minutes, the microscope slides were taken out of the casein solution and dried at 20° C. Thereafter, 2 of the 4 glass microscope slides, one with enzyme and one without enzyme, were washed with deionized water and dried again at 20° C. The other two glass microscope slides were not washed.

All 4 glass microscope slides were examined by means of electron microscopy by using a Zeiss "Neon 40" scanning electron microscope equipped with an EDX detector. SEM images were obtained through use of the InLens detector (secondary electrons) and of the SE detector (secondary and backscattered electrons) at an accelerating voltage of 2 kV. The two nonwashed samples exhibited a continuous coating and had NaCl crystals on the surface, which crystals originated from the enzyme solution used and the pH adjustment with HCl and NaOH. By contrast, the washed glass microscope slide without enzyme no longer had a coating. The conventionally dried-out casein layer was rinsed off as expected. The washed glass microscope slide with enzyme exhibited again a continuous coating with a casein film, whereas the salt crystals and any noncleaved casein present was washed off.

This shows that, in contrast to the conventionally dried-out casein layer, the casein layer deposited with enzymatic cleavage had a higher water resistance and remained stable on the surface. This is attributed to a relatively high hydrophobicity of the enzymatically deposited part of the casein protein.

EXAMPLE 3

Determination of the Hydrophobicity of the Casein Coating

Glass microscope slides (Carl Roth) were cleaned with a mixture of 70% to 30% (v/v) of sulfuric acid to hydrogen peroxide and washed with deionized water. Thereafter, a solution of 1.7 mg/ml chymosin in deionized water was dripped onto the surface of one cleaned glass microscope slide and dried at 20° C. The glass microscope slide containing the adsorbed chymosin was subsequently placed into an aqueous casein solution of a concentration of 10 g/L casein at pH 3 and 40° C. After 60 minutes, the microscope slide was taken out of the casein solution, washed with deionized water and dried. An aqueous casein solution of a concentration of 10 g/L casein, pH 3, was dripped onto the surface of a further cleaned glass microscope slide and dried at 40° C.

Thereafter, the hydrophobicity of the enzymatically applied and the conventionally applied casein coatings was determined in comparison with the hydrophobicity of the pure glass surface via a measurement of the contact angle of water on the particular coating. The contact angle measurements of sessile drops of deionized water were determined using a "Kontaktwinkel-Messsystem G10" [Contact angle measurement system G10] (KRÜSS). The contact angle was measured one second after placement of the drops on the particular slide. Table 1 below shows the measured contact angles. The reported contact angles are in each case mean values from three individual measurements.

TABLE 1

Contact angles

| Sample | Contact angle [°] |
|---|---|
| Cleaned glass surface | 15.5 ± 1.5 |
| Conventionally dripped casein layer | 54.7 ± 8.7 |
| Enzymatically catalytically applied casein layer | 75.3 ± 1.1 |

Table 1 shows that the contact angle of the enzymatically applied coating of cleaved casein is approx. 20° above the value of the contact angle of the dripped coating containing noncleaved casein. The high standard deviation in the case of the noncleaved casein can be attributed to a partial dissolution of the film during the measurement. This confirms the relatively high hydrophobicity of the enzymatically applied casein coating.

EXAMPLE 4

Formation of a Casein Layer by Means of Covalent Immobilization of Chymosin on Glass Surfaces Glass microscope slides (Carl Roth) were cleaned with a mixture of 70% to 30% (v/v) of sulfuric acid to hydrogen peroxide and washed with deionized water. For a covalent immobilization of chymosin on the glass surface, said surface was first functionalized with epoxy groups. To this end, a 10% (w/w) solution of 3-glycidoxypropyltrimethoxysilane (GOPS) in an 80/20 (w/w) mixture of ethanol (EtOH) and water was prepared under alkaline conditions using 1% (w/w) triethylamine (TEA). The glass microscope slides were dipped into the solution and the reaction mixture was carefully stirred at room temperature (20±2° C.) for 1 hour and then left to stand unstirred for a further 10 minutes. Thereafter, the cover slips were rinsed with ethanol in order to remove nonspecifically adsorbed 3-glycidoxypropyltrimethoxysilane. The glasses were then hardened in an oven at 110° C. for 1 hour, rinsed with copious amounts of ethanol and deionized water, left to dry in a fume hood and stored in a desiccator.

For the immobilization, 6 mg of chymosin formulation (Sigma-Aldrich) were dissolved in 100 ml of reaction buffer, a mixture of 1 part phosphate buffer (Sigma-Aldrich) and 19 parts deionized water, pH 7.4. The immobilization reaction was carried out under gentle stirring at room temperature. The progress of the immobilization was followed by the removal of samples (500 µl) of the supernatant of the solution, which were subsequently mixed with 500 µl of a 1% (w/v) hemoglobin solution in reaction buffer (sodium hydrogenphosphate/citric acid, pH=3) in order to determine the enzyme activity. The reaction of the chymosin with hemoglobin was carried out in a water bath at 40° C. for 30 min at pH 3.5, and then stopped by addition of 500 µl of 10% (w/v) trichloroacetic acid solution. Thereafter, the samples were centrifuged at 13 000 rpm for 15 min and, after the centrifugation, the absorbance of the supernatant was measured at 325 nm in comparison with control hemoglobin samples. After 4 days, the immobilization process was stopped and the glass microscope slides were rinsed with deionized water and stored in a desiccator.

The glass microscope slides containing covalently bonded chymosin were placed into an aqueous casein solution of a concentration of 10 g/L casein at pH 3 and 40° C. After 60 minutes, the microscope slide was removed, washed with deionized water and dried.

Glass microscope slides containing chymosin covalently bonded to the epoxy-functionalized surface and glass microscope slides containing casein deposited thereon were examined by means of electron microscopy by using a Zeiss "Neon 40" scanning electron microscope equipped with an EDX detector. Images of the samples were obtained through use of the InLens detector (secondary electrons) and of the SE detector (secondary and backscattered electrons) at an accelerating voltage of 2 kV.

Figure 2:
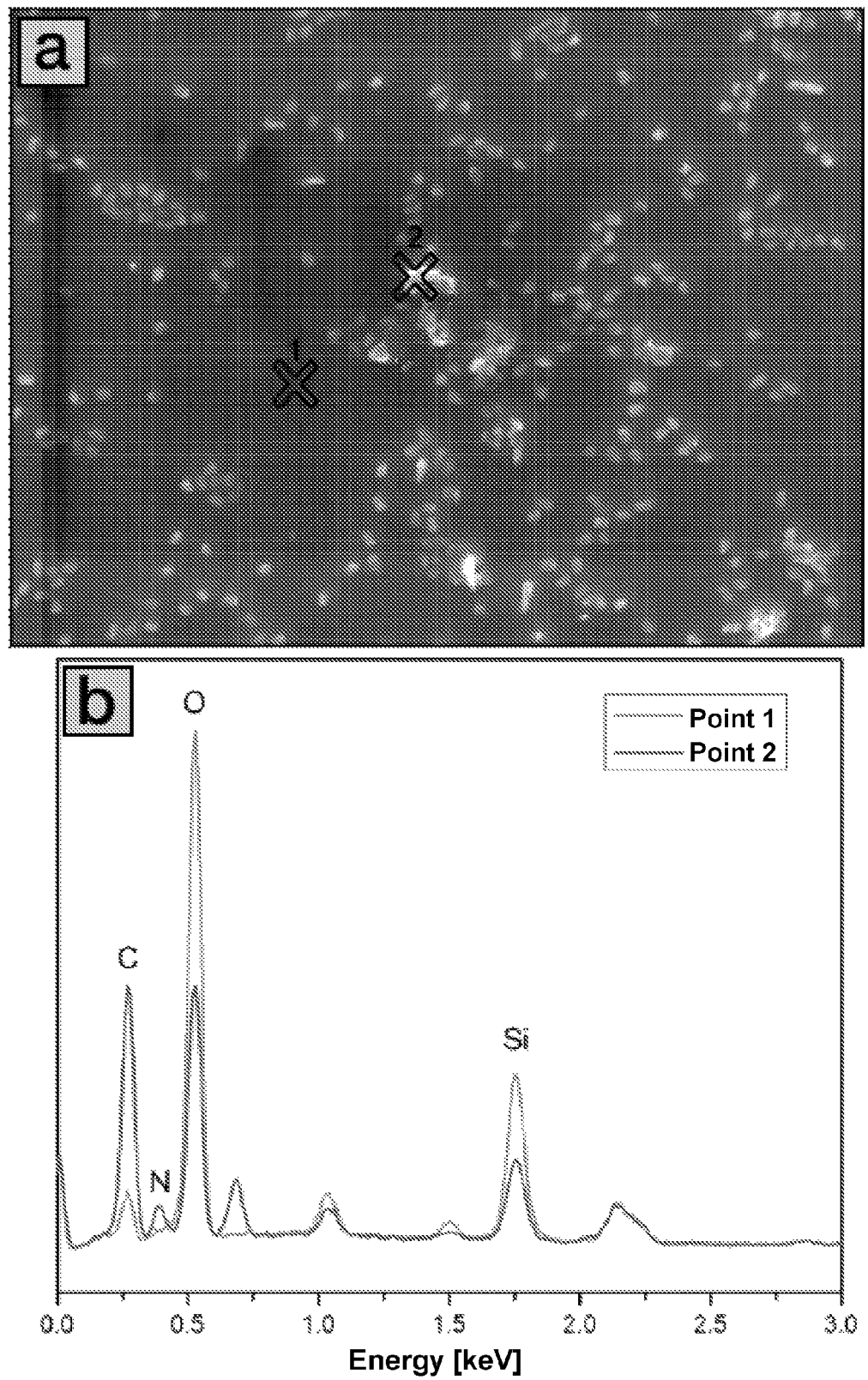

The SEM images of the surface after the enzyme immobilization showed regions having particulate structures of about 500 nm in size, which were assumed to be agglomerated enzyme. To confirm this assumption, EDX measurements of the pure surface and of the regions of the suspected enzyme deposition were carried out. FIG. 2 shows the EDX/SEM determinations. Here, FIG. 2a shows the SEM image of the surface. Point 1 indicates a region of the uncoated surface and point 2 indicates a region of suspected enzyme deposition. FIG. 2b shows the EDX spectra of points 1 and 2. The spectrum of the measurement point 1 exhibited an oxygen/silicon ratio of about 2:1 and traces of carbon. These were attributed to the siloxane functionalization. The suspected enzyme regions exhibited a high carbon fraction and it was additionally possible to detect nitrogen. The ratio of the elements was consistent with protein structures and confirmed the presence of chymosin on the surface.

Figure 3:
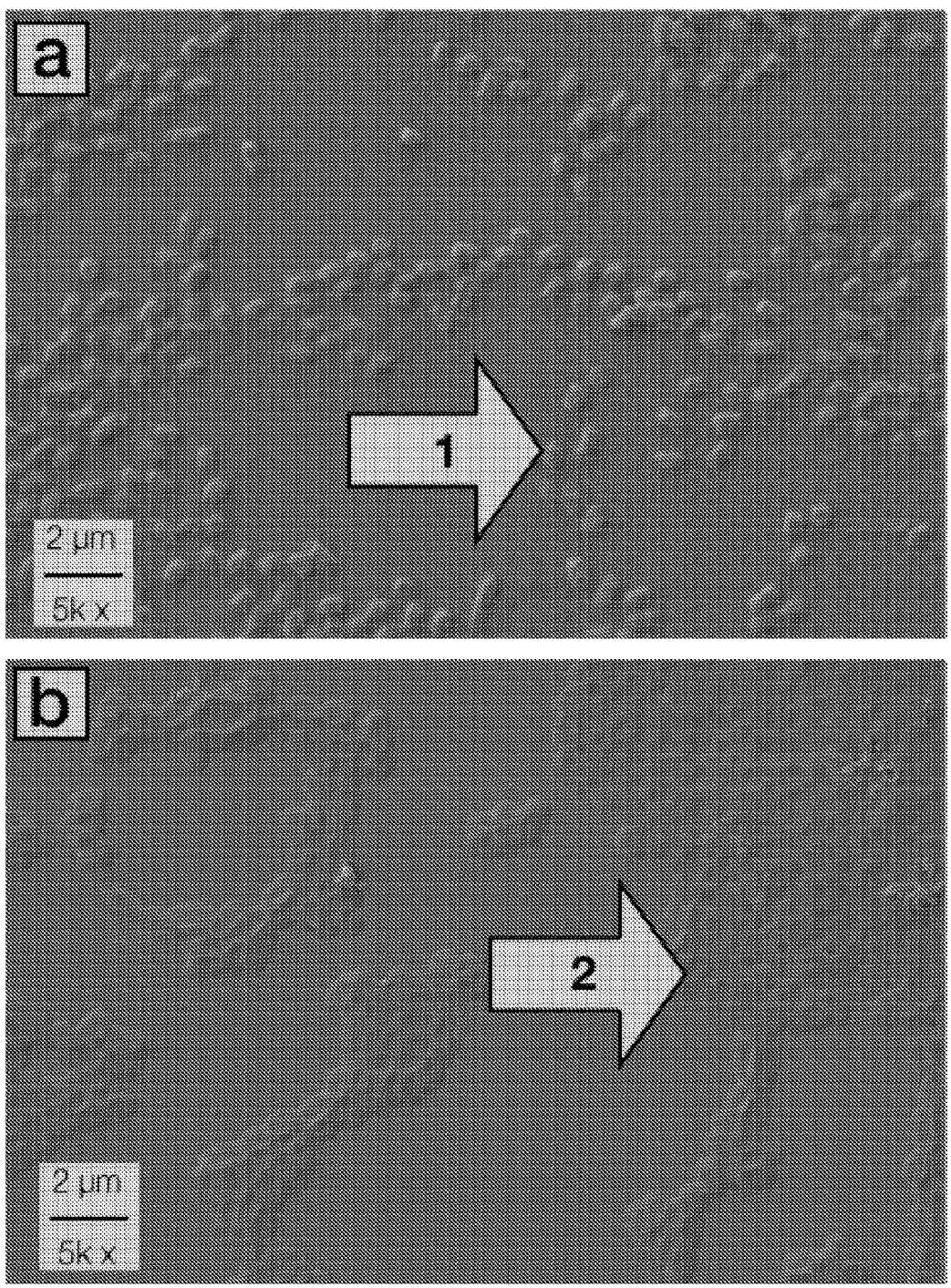
FIG. 3 shows SEM images of the surface of a glass slide containing immobilized chymosin in FIG. 3a, and after the deposition of casein on regions of immobilized chymosin in FIG. 3b.

The SEM images of the surface of the glass slide that are shown in FIG. 3 showed, in FIG. 3a, particulate structures of covalently immobilized chymosin, with a particulate structure being indicated by an arrow 1, and, in FIG. 3b, a specific coating of the regions of immobilized enzyme as a result of deposition of casein on the enzyme, with the remaining regions of the surface remaining uncoated. A region of casein deposited on the enzyme is indicated by an arrow 2. There was deposition of a very thin casein film, below which the particulate structures of the immobilized chymosin still remained easily identifiable. It is therefore assumed that on the enzyme covalently bonded on the surface had merely formed a monomicellar layer of casein. It is suspected that the deposited cleaved casein covers the enzyme and thus prevents further reactions in this specific region.

This result shows that the activity of the enzyme covalently bonded to the surface is sufficient to catalyze the cleavage reaction and to provide the possibility of specific partial protein coatings.

EXAMPLE 5

Deposition of a coating solution containing casein and titanium dioxide by means of adsorbed enzyme on a glass slide 2 g of $TiO_2$ (Sigma-Aldrich) were dispersed in 100 mL of an aqueous casein solution having a concentration of 10 g/L casein, pH 3, the particles having an estimated size within the range from 200 nm to 400 nm. The dispersion was done at 700 rpm in a dissolver for 30 minutes.

Glass microscope slides were cleaned with a mixture of 70% to 30% (v/v) of sulfuric acid to hydrogen peroxide and washed with deionized water. Thereafter, a solution of 1.7 mg/ml chymosin, based on the pure enzyme, in deionized water was dripped onto the surface and dried at 20° C.

Thereafter, the dispersion was deposited on the glass microscope slide containing adsorbed chymosin, by the glass microscope slide being placed into the casein solution containing dispersed $TiO_2$ at 40° C. for 60 minutes. Afterwards, the microscope slide was removed from the casein solution, washed with deionized water and dried.

Figure 4:
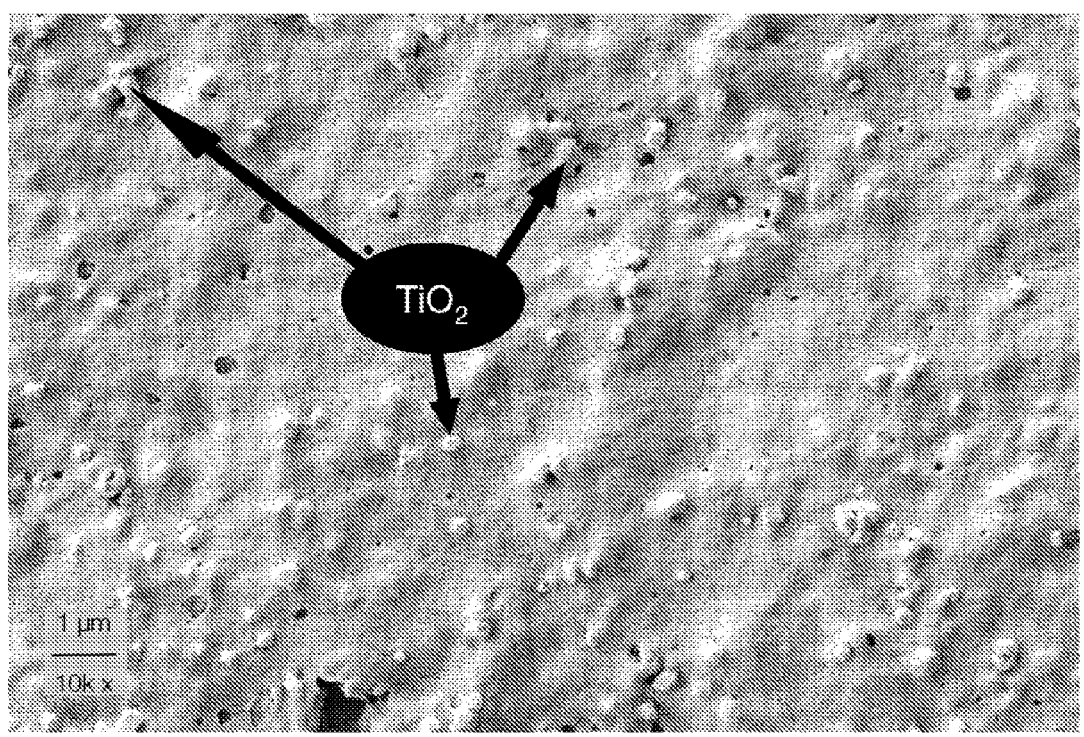
FIG. 4 shows an SEM image of the surface of a glass slide containing a coating applied from an aqueous casein solution containing 10 g/L casein containing dispersed titanium dioxide particles.

The casein film obtained was examined by means of electron microscopy. FIG. 4 shows the SEM images of the applied casein layer. The SEM image shown in FIG. 4 showed a continuous coating having a whitish color. Furthermore, the coating had particulate structures, which were attributed to casein-coated titanium dioxide particles. It was assumed that the dispersed titanium dioxide particles were enveloped by casein and deposited.

This result shows that the method according to the invention also makes it possible to deposit coating solutions containing casein and customary paint components such as titanium dioxide.

Altogether, the examples show that it is possible to apply the enzyme by means of physical adsorption or covalent bonding to the surface, it being possible to deposit relatively thick coatings of controlled layer thicknesses by means of physical adsorption, whereas enzyme covalently bonded to the surface offers the possibility of partial protein coatings.

EXAMPLE 6

Deposition of Small-Area Enzyme Aggregates by Means of Covalent Immobilization of Chymosin Glass microscope slides (VWR) were cleaned as described in Example 4 with a mixture of sulfuric acid and hydrogen peroxide and epoxy-functionalized with a 10% solution of 3-glycidoxypropyltrimethoxysilane (GOPS). Thereafter, nonspecifically adsorbed GOPS was removed and the coated glass surface was hardened at 110° C. for 1 hour.

Chymosin in the form of rennet powder was purchased from RENCO NEW ZEALAND via the European supplier BICHSEL AG (Switzerland). According to the information from the manufacturer, the proportion of chymosin was 5% (w/w). To increase the proportion of chymosin and thus the efficiency of the enzymatic reaction, the salt content was reduced by ultrafiltration. For this purpose, the rennet powder was dissolved in deionized water and centrifuged three times for two hours at 5000× g and 25° C. across Amicon® Ultra-15 centrifugal filter units up to a proportion of chymosin of 67% (w/w).

Chymosin solutions of an enzyme quantity of 60 µg/mL were prepared in 25 mM and 1 M phosphate buffer solutions at pH 7.4 and immobilized on the coated glass microscope slides at room temperature for 93 h, the activity being measured as described in Example 4.

Figure 5:
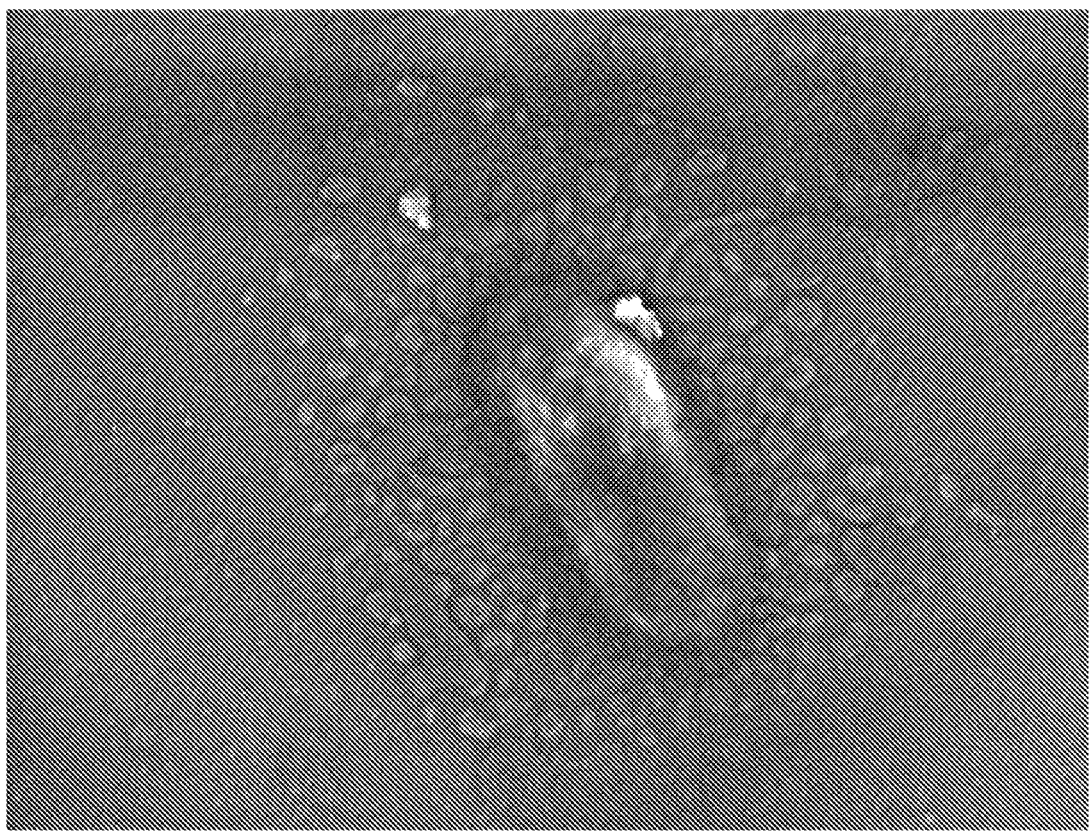
FIG. 5 shows an SEM image of a glass microscope slide which has been coated with chymosin solution.

The glass microscope slides containing covalently bonded chymosin were placed into an aqueous casein solution of a concentration of 10 g/L casein at pH 3 and 40° C. After 60 minutes, the microscope slide was removed, washed with deionized water and dried. The casein coatings obtained were examined by means of electron microscopy (SEM) by using a Zeiss "Neon 40" scanning electron microscope. Images of the samples were recorded by using the SE2 detector at high topographic contrast at an accelerating voltage of 2 kV. FIG. 5 shows an SEM image of a glass microscope slide coated with chymosin in a 25 mM phosphate buffer solution. It was determined that enzyme aggregates of approx. 500 nm in size were formed on said glass slides, which aggregates initiate a deposition of individual particles of casein when the aggregates were present in isolation. As further shown by FIG. 5, a deposition of individual casein micelles within a distance of <1 µm around the enzyme aggregates was observed. In the case of the glass slides coated with chymosin in a 1 M phosphate buffer solution, very much smaller enzyme agglomerates having a size of approx. 15 nm to 25 nm were bound. This shows that larger or smaller aggregates were formed depending on the ionic strength present due to the variable buffer concentration. In this connection, it was possible to achieve smaller aggregates in the case of higher ionic strengths.

EXAMPLE 7

Covalent Bonding of the Enzyme to the Surface Via Glutaraldehyde

Glass microscope slides (VWR) cleaned with sulfuric acid and hydrogen peroxide were amino-functionalized. To this end, a 10% (w/w) solution of aminopropyltriethoxysilane (APS) in an 80:20 (w/w) mixture of ethanol (EtOH) and water was prepared under neutral conditions. The glass microscope slides were dipped into the solution at room temperature (20±2° C.) for 2 hours. Thereafter, rinsing was carried out with ethanol in order to remove nonspecifically adsorbed APS. The glasses were then hardened in an oven at 110° C. for 1 hour, rinsed with copious amounts of ethanol and deionized water, left to dry in a fume hood and stored in a desiccator until further use. In a second step, these APS-activated glass slides were incubated at room temperature (20±2° C.) for 17 hours with a 15% (w/w) solution of glutaraldehyde in a mixture of 1 part phosphate buffer (Sigma-Aldrich) and 19 parts deionized water, pH 7.4, resulting in the presence of a terminal aldehyde group.

A chymosin solution of a concentration of 60 µg/mL in a mixture of 1 part phosphate buffer and 19 parts deionized water, pH 7.4, was prepared and immobilized on the coated glass microscope slides at room temperature for 24 h, the activity being monitored as described in Example 4.

The glass microscope slides containing covalently bonded chymosin were placed into an aqueous casein solution of a concentration of 10 g/L casein at pH 3 and 40° C. After 60 minutes, the microscope slide was removed, washed with deionized water and dried. The casein coatings obtained were examined by means of electron microscopy (SEM).

It was determined that a more continuous enzyme distribution was formed on the amino-functionalized surface of the glass slides. The formation of small aggregates of approx. 50 nm is attributed to the immobilization technique used. A film-type, very thin monolayer of casein was deposited onto these the enzyme aggregates not present in isolation.

EXAMPLE 8

Covalent Bonding of the Enzyme to the Surface Via Polyethylene Glycol as Polymeric Spacer Cleaned glass microscope slides were amino-functionalized with aminopropyltriethoxysilane (APS) as described in Example 7. In a second step, these APS-activated glass slides were incubated at room temperature (20±2° C.) for 24 hours with a 0.25 g/L solution of polyethylene glycol diglycidyl ether ($M_n$=20 000 g/mol, Creative PEGWorks, USA) in 100 mM phosphate buffer. This resulted in a terminal epoxy group being bonded to the glass surface via polyethylene glycol as polymeric spacer.

A chymosin solution of a concentration of 60 µg/mL in a mixture of 1 part phosphate buffer and 19 parts deionized water, pH 7.4, was prepared and immobilized on the coated glass microscope slides at room temperature for 24 h, the activity being monitored as described in Example 4.

The glass microscope slides containing covalently bonded chymosin were placed into an aqueous casein solution of a concentration of 10 g/L casein at pH 3 and 40° C. After 60 minutes, the microscope slide was removed, washed with deionized water and dried. The casein coating obtained was examined by means of electron microscopy (SEM).

It was determined that the enzyme was successfully bonded to the glass surface via polyethylene glycol as polymeric spacer. Furthermore, it was observed that the use of the spacer under the described conditions gave rise to hybrid structures, observance being made of an inner "ring" having a continuous, film-type casein deposition and, additionally, a deposition of individual micelles, i.e., of individual particles, in an outer "ring".

EXAMPLE 9

Adhesive Bonding of Glass Microscope Slides Via Cleaved Casein

Chymosin in the form of rennet powder was purchased from RENCO NEW ZEALAND via the European supplier BICHSEL AG (Switzerland). According to the information from the manufacturer, the proportion of chymosin was 5% (w/w). To increase the proportion of chymosin and thus the efficiency of the enzymatic reaction, the salt content was reduced by ultrafiltration. For this purpose, the rennet powder was dissolved in deionized water and centrifuged three times for two hours at 5000×g and 25° C. across Amicon® Ultra-15 centrifugal filter units up to a proportion of chymosin of 67% (w/w).

Glass microscope slides (VWR) were cleaned with ethyl acetate in an ultrasonic bath for 45 minutes and washed with deionized water. 625 µl of an aqueous solution of chymosin of a concentration of 25 g/L were dripped onto an area of 25×25 mm² of the glass microscope slides and dried. Thereafter, two glass microscope slides at a time containing adsorbed chymosin were fixed in holders, with spacers of a thickness of 125 µm being used in order to establish various distances of 125 µm, 250 µm, 375 µm or 500 µm between the particular glass microscope slides. After fixation, the spacers were removed. Thereafter, the two glass microscope slides were immersed into 200 ml of a casein dispersion having concentrations of 1 g/L, 5 g/L, 10 g/L or 20 g/L at 40° C. for 80 minutes. After the cleavage reaction, the glass microscope slides adhering together were washed with deionized water and dried.

An adhesion was rated as successful when the glass microscope slides held together both after the removal of the holders and also after manual application of slight mechanical stress.

Table 2 below shows the results of the adhesion for the various distances and casein concentrations. The reported results are in each case mean values from three individual measurements.

TABLE 2

Results of the adhesion experiments

| Distance [µm] | Casein concentration [g/L] | Chymosin concentration [g/L] | pH | Result |
|---|---|---|---|---|
| 125 | 20 | 25 | 3 | + |
| 250 | 20 | 25 | 3 | + |
| 375 | 20 | 25 | 3 | + |
| 500 | 20 | 25 | 3 | − |
| 250 | 20 | 25 | 3 | + |
| 250 | 10 | 25 | 3 | + |
| 250 | 5 | 25 | 3 | +/− |
| 250 | 1 | 25 | 3 | − |
| 250 | 20 | No enzyme | 3 | − |
| 250 | 20 | Only NaCl | 3 | − |
| 250 | 20 | 25 | 12 | − |

It can be seen from Table 2 that it was possible to determine a successful bonding-together of the two glass microscope slides up to a distance of 375 µm. Samples at a distance of 500 µm no longer bonded together. Here, a detachment of the precipitated casein from the subsurface was visually determined at large distances. Moist precipitated casein is still very soft and flexible. It is therefore assumed that the material detaches from the subsurface owing to gravity when the applied layer becomes too heavy. However, when two layers are brought together before there is a detachment of a layer, the adhesive-bonding process was successful. If the distance is too great, the layers cannot come together and it is not possible to achieve an adhesive bonding.

Furthermore, the concentration of the casein solution was investigated as a parameter. It was determined that concentrations of 20 g/L and 10 g/L both adhesively bonded the microscope slides. A concentration of 5 g/L showed variable results and was considered to be a kind of threshold. Lower concentrations of 1 g/L no longer showed any bonding-together of the microscope slides. In the successful experiments, a bonding-together was only observed in the lower regions of the microscope slides which were functionalized with enzyme. This observation supports the assumption of the enzymatic reaction being the driving force of the process. Blank tests were carried out in order to evidence the need for the enzymatic reaction for the adhesive bonding. When the experiments were carried out without enzyme, adhesive bonding of the microscope slides was not observed. Similarly, there was no adhesive bonding when the enzyme was deactivated at a pH of 12. To rule out a deposition of casein due to salt effects, a sodium chloride solution instead of the enzyme solution was dried on the microscope slides as a further control sample, and adhesive bonding was likewise not determined. Salt effects were ruled out as a control because the chymosin used was formulated with NaCl in order to increase its long-term stability. Although the salt content was reduced from 95% to 33% prior to use, there was still the presence of a significant proportion of salt, which can induce a deposition of protein. However, it was determined that such a deposition is not sufficient for an adhesive bonding. Altogether, the controls thus provide clear evidence that the adhesive bonding was triggered by the enzymatic reaction.

Figure 6:
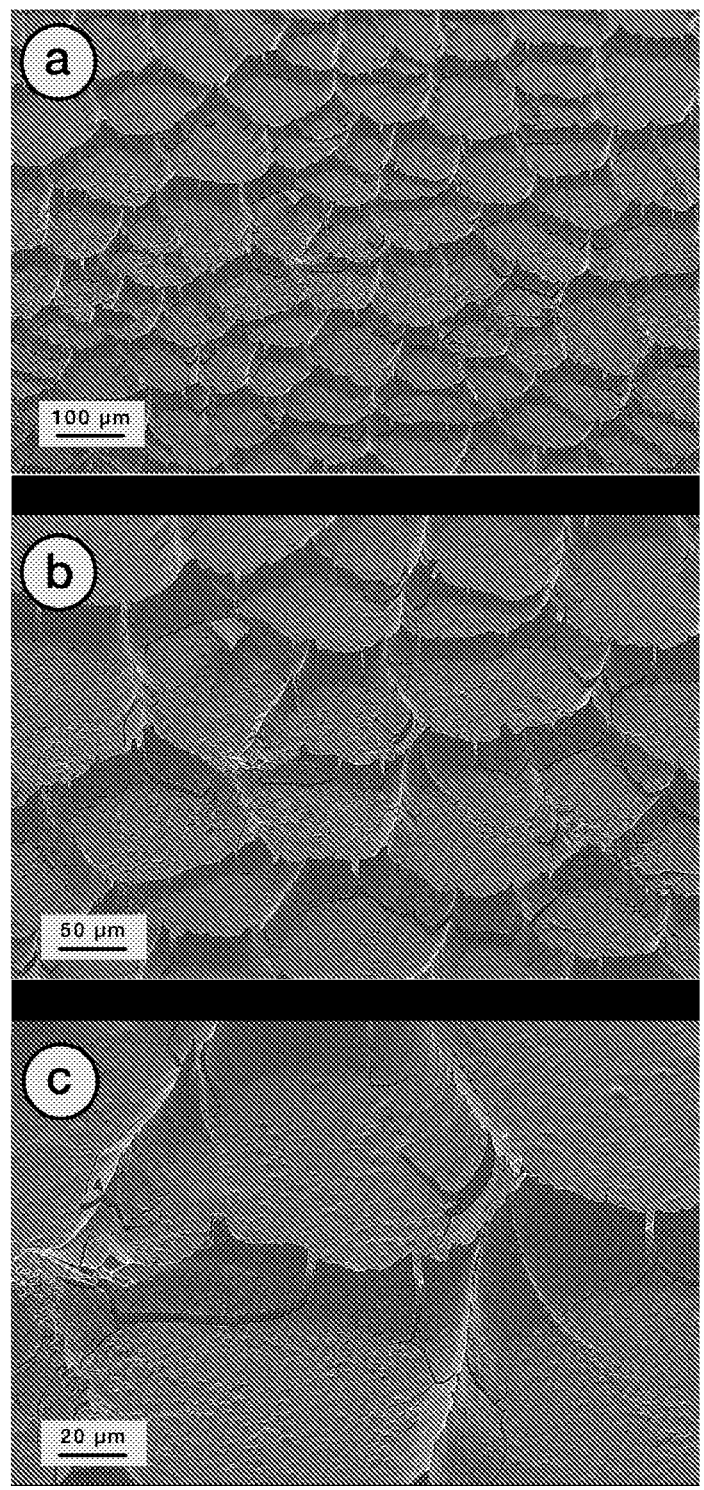
FIG. 6 shows an SEM image of a glass microscope slide after adhesive bonding with an aqueous casein solution.

Furthermore, the adhesive casein coatings obtained after a separation of the particular adhesively bonded microscope slides were examined by means of electron microscopy (SEM) by using a Zeiss "Neon 40" scanning electron microscope. Images of the samples were recorded by using the SE2 detector at high topographic contrast at an accelerating voltage of 2 kV. FIG. 6 shows the SEM images of a glass microscope slide after the adhesive bonding. As can be seen in FIGS. 6a, b and c, a continuous casein layer was formed in each case on the glass microscope slides, which layer covers the entire surface of the slide. Furthermore, a honeycombed structure was formed on the continuous coating, the edges of said structure becoming thinner with increasing height. Said structure was found in each case on both microscope slides. This suggests that the casein formed a coating on both sides, which are connected by a complex pattern of walls. It is assumed that such a structure is formed because, firstly, a solid layer cannot be formed owing to an insufficient availability of casein. Furthermore, the angle of three walls branching out was frequently about 120°, which indicates that the formation of the honeycombed structures occurs owing to the different polarity of the hydrophobic cleaved casein and of the hydrophilic water. Furthermore, the casein cures during the drying process and shrinks, and, as a result, the thickness of the side edges becomes a function of the distance from the particular microscope slide.

This example shows that glass surfaces can be adhesively bonded to one another by means of the method according to the invention. An adhesive bonding via application of chymosin and deposition of casein was likewise repeated under the described conditions on steel surfaces. It was determined that the steel surfaces also adhesively bonded to one another. This shows that metal surfaces can likewise be adhesively bonded to one another by means of the method according to the invention.

As a result of application of the enzyme chymosin followed by the deposition of the cleavage product of the biopolymer used, a casein layer connecting two objects was formed between said objects. This allows applications for biomaterials, for example for medical applications such as medical implants, or as biodegradable adhesives.

The invention claimed is:

1. A method for coating surfaces by enzymatic reaction of a biopolymer, the biopolymer being casein, the method comprising:
   a) applying an enzyme to the surface of a substrate, wherein the enzyme is a protease selected from the group consisting of chymosin and pepsin, and
   b) contacting the protease with casein, the protease cleaving the casein, the cleavage giving rise to at least two cleavage products of casein having differing solubility in a solvent, and at least one cleavage product of casein having relatively low solubility being deposited on the surface of the substrate.

2. The method as claimed in claim 1, wherein the enzyme is applied to the surface by means of physical adsorption, or ionic, coordinate or covalent bonding, it being possible to effect the covalent bonding to the surface via a polymeric spacer.

3. The method as claimed in claim 1, wherein the enzyme is applied to the surface in a full-area or partial manner.

4. The method as claimed in claim 1, wherein
   the biopolymer to be deposited is present in aqueous solution, the concentration of the biopolymer in the solution being within the range from ≥0.01 g/L to ≤50 g/L, and/or
   the reaction time between biopolymer and enzyme is within the range from ≥1 min to ≤240 min, and/or
   the temperature of the deposition reaction is within the range from ≥0° C. to ≤50° C.

5. The method as claimed in claim 1, wherein a coating having a layer thickness within the range from ≥10 nm to ≤50 μm is applied.

6. A coated article obtainable by means of the method as claimed in claim 1, wherein the article comprises a casein coating formed of casein micelles, a hydrophilic part of κ-casein having been cleaved off at a site of a phenylalaninel$^{105}$-methioninel$^{106}$ bond.

7. The method as claimed in claim 2, wherein the polymeric spacer is selected from the group comprising polyethylene glycol, polyvinyl alcohol, polyesters, and/or dextrans.

8. The method as claimed in claim 4, wherein
   the concentration of the biopolymer in the solution is within the range from ≥0.1 g/L to ≤10 g/L, and/or
   the reaction time between biopolymer and enzyme is within the range from ≥5 min to ≤60 min, and/or
   the temperature of the deposition reaction is within the range from ≥30° C. to ≤40° C.

9. The method as claimed in claim 5, wherein the coating has a layer thickness within a range from ≥20 nm to ≤1 μm.

10. The method as claimed in claim 1, wherein the contacting step is performed by adding the protease to the casein in an acidic solution.

11. The coated article as claimed in claim 6, wherein the article is a medical implant, a biodegradable material, an edible material, a colloidal particle, or a surface to be adhesively bonded.

* * * * *